United States Patent
Carree

(10) Patent No.: US 10,015,949 B2
(45) Date of Patent: Jul. 10, 2018

(54) HYBRID SWISS CHARD VARIETY 69-104 RZ

(71) Applicant: RIJK ZWAAN ZAADTEELT EN ZAADHANDEL B.V., De Lier (NL)

(72) Inventor: Franciscus Hermanus Carree, De Lier (NL)

(73) Assignee: RIJK ZWAAN ZAADTEELT EN ZAADHANDEL B.V., De Lier (NL)

(*) Notice: Subject to any disclaimer, the term of this patent is extended or adjusted under 35 U.S.C. 154(b) by 0 days.

(21) Appl. No.: 15/466,971

(22) Filed: Mar. 23, 2017

(65) Prior Publication Data

US 2017/0280668 A1 Oct. 5, 2017

Related U.S. Application Data

(60) Provisional application No. 62/314,518, filed on Mar. 29, 2016.

(51) Int. Cl.
*A01H 5/12* (2018.01)
*C12Q 1/6895* (2018.01)

(52) U.S. Cl.
CPC ............ *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

Pokluda et al 2002 Hortacultural Science 29(3): 114-118.*

* cited by examiner

*Primary Examiner* — David H Kruse
(74) *Attorney, Agent, or Firm* — Duane Morris LLP; Thomas J. Kowalski; Deborah L. Lu

(57) ABSTRACT

The present invention relates to a hybrid Swiss chard seed designated 69-104 RZ. The present invention also relates to a Swiss chard plant produced by growing the 69-104 RZ seed, which plant exhibits a combination of traits including green leaves with a reddish purple petiole and midrib, slow growing, resistance to downy mildew (*Peronospora farinosa* f sp. *betae*), a dark to very dark green leaf coloring and strongly blistered leaf blades. The invention further relates to methods for producing the Swiss chard cultivar, represented by hybrid Swiss chard variety 69-104 RZ.

24 Claims, No Drawings

HYBRID SWISS CHARD VARIETY 69-104 RZ

RELATED APPLICATIONS AND INCORPORATION BY REFERENCE

This application claims priority to U.S. provisional patent application Ser. No. 62/314,518, filed Mar. 29, 2016.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated herein by reference, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new hybrid Swiss chard (*Beta vulgaris*) variety which exhibits a combination of traits including green leaves with a reddish purple petiole and midrib, slow growing, resistance to downy mildew (*Peronospora farinosa* f. sp. *betae*), a dark to very dark green leaf coloring and strongly blistered leaf blades.

BACKGROUND OF THE INVENTION

Swiss chard (*Beta vulgaris*) is a leafy vegetable belonging to the family Amaranthaceae. All cultivated *Beta vulgaris* varieties fall into the subspecies *Beta vulgaris* subsp. *vulgaris*. The wild ancestor of these cultivated varieties is *Beta vulgaris* subsp. *maritima*, commonly known as the sea beet, and is found throughout the Mediterranean, the Atlantic coast of Europe, the Near East, and India. *Beta vulgaris* has four different cultivated forms: the common garden beet, also called beetroot or table beet, is a vegetable grown for its roots; the sugar beet is used to produce sugar; mangelwurzel is a fodder crop; and Swiss chard, also known as chard, leaf beet or silverbeet, is grown for its nutrient-rich leaves. Though nowadays the generally accepted name for Swiss chard is *Beta vulgaris* subsp. *vulgaris*, its taxonomic rank has changed many times, and Swiss chard is also occasionally indicated as *Beta vulgaris* var. *vulgaris* or *Beta vulgaris* var. *cicla*.

Swiss chard leaves are an excellent source of vitamins such as A, C, and K, and a good source of minerals such as iron, magnesium and potassium. Fresh young "baby leaf" Swiss chard can be used raw in salads, while mature Swiss chard leaves and stalks are typically cooked or sautéed. Swiss chard is not only a healthy but also an attractive leafy vegetable, with a lot of variation in coloring. Depending on the variety the leaf blade may be green, dark green or reddish in color, while the petiole (also called the leaf stalk) and major veins (midrib and secondary veins) of the leaf may be white, green, yellow, orange, red or even purple. The yellow to reddish-purple colors are caused by the presence of different betalain pigments. There are two classes of betalains: (a) betacyanins that include the reddish to violet betalain pigments and (b) betaxanthins that include the yellow to orange betalain pigments.

Swiss chard leaves may show weak to strong blistering of the leaf blade. Strong blistering of the leaf blade is preferred in the fresh market because those leaves pack looser than leaf varieties with weak or medium blistering of the leaf blade and are less likely to wilt or turn yellow.

Downy mildew is a harmful disease that may cause serious losses to Swiss chard crops. Since young leaves are particularly affected, this can be a major issue in Swiss chard "baby leaf" production. The causal agent of downy mildew on various Amaranthaceae, including Swiss chard, is regarded as a single species, *Peronospora farinosa*. In particular, *Peronospora farinosa* f. sp. *betae* (formerly called *Peronospora schactii*) infects Swiss chard. Initial symptoms of downy mildew consist of light green leaf spots on the upper leaf surfaces. Under moist conditions an initially whitish and then dull to violet-gray hyphal growth appears on the lower surface and sometimes upper surface of the leaves and sporangia become visible. Affected leaves may wilt and die. Since cotyledons and young leaves are particularly affected, this can be a major issue in Swiss chard "baby leaf" production. In older Swiss chard plants the growing point may become infected and may cause the leaves to become thickened, distorted, light green and often twisted with downward-curled margins. Flower parts may also be infected, causing mycelium and oospores to develop within seed clusters. Under favorable conditions the infection can spread very rapidly, resulting in widespread crop damage. The optimal temperature for formation and germination of *P. farinosa* f. sp. *betae* spores is around 12° C., and it is facilitated by a high relative humidity greater than 85%. When spores are deposited on a humid leaf surface they can readily germinate and infect the leaf. The optimum temperature range for infection is 7-15° C. The disease incubation period ranges from 4 to 32 days, depending on environmental conditions. *Peronospora farinosa* f. sp. *betae* survives as oospores and mycelium in crop residues, in wild and volunteer *Beta* species, and in seeds. Although some fungicide treatments may be effective, they are costly and cause ecological pollution.

*Cercospora* leaf spot, caused by the pathogen *Cercospora beticola* is one of the most important diseases that infects Swiss chard, and can also grow on many weed species, spinach and most wild *Beta* species. Initial symptoms are small, angular leaf spots that are brown or tan with purple to red borders. Lesions at maturity appear gray-colored to dark tan with a brown to purple border. In severe cases the spots can coalesce and cause large sections or entire leaves to die. Cercopora leaf spot may be recognized by the presence of tiny black dots (pseudostromata) that form in lead substomatal cavities with grayish-tan lesions. These pseudostromata produce conidiophores that bear the spores of *Cercospora beticola*. The pathogen survives mainly in plant debris, but can also survive in seeds. When moisture is sufficient, new spores are formed and spread via rain-splash and wind to new leaves or plants. *Cercospora* leaf spot can result in significant losses, especially in late summer when conditions are favorable (high temperatures, high humidity, long leaf wetness periods at night) as infected Swiss chard leaves become unmarketable. Although fungicide treatment may be effective, this must be considered carefully as *C. beticola* populations have been known to develop a resistance to major classes of fungicides.

Citation or identification of any document in this application is not an admission that such document is available as prior art to the present invention.

SUMMARY OF THE INVENTION

There exists a need, therefore, for a hybrid Swiss chard variety which exhibits a combination of traits including green leaves with a reddish purple petiole and midrib, slow growing, resistance to downy mildew (*Peronospora farinosa* f. sp. *betae*), a dark to very dark green leaf coloring and strongly blistered leaf blades.

The present invention addresses this need by providing a new type of Swiss chard (*Beta vulgaris*) variety, designated 69-104 RZ. Swiss chard cultivar 69-104 RZ exhibits a combination of traits including green leaves with a reddish purple petiole and midrib, slow growing, resistance to downy mildew (*Peronospora farinosa* f. sp. *betae*), a dark to very dark green leaf coloring and strongly blistered leaf blades.

The present invention provides a seed of Swiss chard variety 69-104 RZ, a sample of seed of said hybrid variety having been deposited with the National Collections of Industrial, Marine and Food Bacteria (NCIMB) in Bucksburn, Aberdeen AB21 9YA, Scotland, UK and have been assigned NCIMB Accession No. 42561.

The invention further relates to a plant grown from said seed of hybrid Swiss chard variety 69-104 RZ.

In one embodiment, the invention relates to a plant grown from said seed of hybrid Swiss chard variety 69-104 RZ, which is a plant grown from seed having been deposited under NCIMB Accession No. 42561.

In one embodiment, the invention provides a Swiss chard plant, or a part thereof, having all the physiological and morphological characteristics of the Swiss chard plant grown from the seed of hybrid Swiss chard variety 69-104 RZ, a sample of seed of said hybrid variety having been deposited under NCIMB Accession Number 42561.

In one embodiment, the invention provides a Swiss chard plant designated 69-104 RZ, representative seed of which have been deposited under NCIMB Accession No. 42561, wherein said Swiss chard plant may comprise a combination of traits including green leaves with a reddish purple petiole and midrib, slow growing, resistance to downy mildew (*Peronospora farinosa* f sp. *betae*), a dark to very dark green leaf coloring and strongly blistered leaf blades.

In one embodiment, the invention provides a Swiss chard plant designated 69-104 RZ, representative seed of which have been deposited under NCIMB Accession No. 42561.

In one embodiment, the invention provides a Swiss chard plant designated 69-104 RZ, representative seed of which have been deposited under NCIMB Accession No. 42561, wherein said Swiss chard plant may comprise the following combination of traits including green leaves with a reddish purple petiole and midrib, slow growing, resistance to downy mildew (*Peronospora farinosa* f sp. *betae*), a dark to very dark green leaf coloring and strongly blistered leaf blades, which is a plant grown from seed having been deposited under NCIMB Accession No. 42561.

In one embodiment, the invention provides a seed capable of growing into of a Swiss chard plant designated 69-104 RZ, representative seed of which having been deposited under NCIMB Accession No. 42561, wherein said plant may comprise at least the following combination of traits including green leaves with a reddish purple petiole and midrib, slow growing, resistance to downy mildew (*Peronospora farinosa* f. sp. *betae*), a dark to very dark green leaf coloring and strongly blistered leaf blades.

In an embodiment of the present invention, there also is provided a part of a Swiss chard plant grown from the seed of hybrid Swiss chard variety 69-104 RZ of the invention, which may include a part of a Swiss chard plant exhibiting a combination of traits including green leaves with a reddish purple petiole and midrib, slow growing, resistance to downy mildew (*Peronospora farinosa* f sp. *betae*), a dark to very dark green leaf coloring and strongly blistered leaf blades, or a part of a Swiss chard plant having any of the aforementioned resistance(s) and a combination of traits including one or more morphological or physiological characteristics tabulated herein, including a part of hybrid Swiss chard variety 69-104 RZ, wherein the plant part is involved in sexual reproduction, which includes without limitation, a microspore, pollen, an ovary, an ovule, an embryo sac or egg cell and/or wherein the plant part is suitable for vegetative reproduction, which includes, without limitation, a cutting, a root, a stem, a cell or a protoplast and/or wherein the plant part is a tissue culture of regenerable cells in which the cells or protoplasts of the tissue culture are derived from a tissue such as, for example and without limitation, a leaf, pollen, an embryo, a cotyledon, a hypocotyl, a meristematic cell, a root, a root tip, an anther, a flower, a seed or a stem. The plants of the invention from which such a part can come include those wherein representative seed of which has been deposited under NCIMB Accession No. 42561 or hybrid Swiss chard variety or cultivar designated 69-104 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In another embodiment there is a plant grown from seeds, representative seed of which having been deposited under NCIMB Accession No. 42561.

In a further embodiment there is a plant regenerated from the above-described plant parts or regenerated from the above-described tissue culture. Advantageously such a plant may have morphological and/or physiological characteristics of hybrid Swiss chard variety 69-104 RZ and/or of a plant grown from seed, representative seed of which having been deposited under NCIMB Accession No. 42561—including without limitation such plants having all of the morphological and physiological characteristics of hybrid Swiss chard variety 69-104 RZ and/or of plant grown from seed, representative seed of which having been deposited under NCIMB Accession No. 42561. Advantageously, such a plant demonstrates the traits of green leaves with a reddish purple petiole and midrib, slow growing, resistance to downy mildew (*Peronospora farinosa* f sp. *betae*), a dark to very dark green leaf coloring and strongly blistered leaf blades.

Accordingly, in still a further embodiment, there is provided a Swiss chard plant having all of the morphological and physiological characteristics of hybrid Swiss chard variety 69-104 RZ, a sample of seed of said hybrid having been deposited under NCIMB Accession No. 42561. Such a plant can be grown from the seeds, regenerated from the above-described plant parts, or regenerated from the above-described tissue culture. A Swiss chard plant having any of the aforementioned resistance(s), and one or more morphological or physiological characteristics recited or tabulated herein, and a Swiss chard plant advantageously having all of the aforementioned resistances and the characteristics recited and tabulated herein, are preferred. Parts of such plants—such as those plant parts above-mentioned—are encompassed by the invention.

In one embodiment of the present invention, there is provided a Swiss chard plant which may comprise genetic information for so exhibiting a combination of traits including green leaves with a reddish purple petiole and midrib, slow growing, resistance to downy mildew (*Peronospora farinosa* f sp. *betae*), a dark to very dark green leaf coloring and strongly blistered leaf blades; wherein the genetic information is as contained in a plant, representative seed of which having been deposited under NCIMB Accession No. 42561.

In one embodiment, the invention relates to a method of vegetatively propagating a plant of hybrid Swiss chard variety 69-104 RZ which may comprise the steps of: (a) collecting tissue capable of being propagated from a plant of hybrid Swiss chard variety 69-104 RZ, representative seed of said hybrid Swiss chard variety having been deposited under NCIMB Accession Number 42561; and (b) producing a rooted plant from said tissue.

In an embodiment of the present invention, there is provided a Swiss chard plant exhibiting a combination of traits which may comprise green leaves with a reddish purple petiole and midrib, slow growing, resistance to downy mildew (*Peronospora farinosa* f sp. *betae*), a dark to very dark green leaf coloring and strongly blistered leaf blades, and having genetic information for so exhibiting the combination of traits; wherein the genetic information is as contained in a plant, representative seed of which having been deposited under NCIMB Accession No. 42561. Parts of such plants—such as those plant parts above-mentioned—are encompassed by the invention.

In one embodiment, there is provided a method for producing a progeny plant of hybrid Swiss chard variety 69-104 RZ which may comprise crossing the plant designated 69-104 RZ with itself or a second Swiss chard plant, harvesting the resultant seed, and growing said seed.

In a further embodiment, there is provided a progeny plant of Swiss chard variety 69-104 RZ produced by sexual or vegetative reproduction, grown from seeds, regenerated from the above-described plant parts, or regenerated from the above-described tissue culture of the Swiss chard cultivar or a progeny plant thereof, representative seed of which having been deposited under NCIMB Accession No. 42561. The progeny plant may have any of the aforementioned resistance(s), and one or more morphological or physiological characteristics recited or tabulated herein, and a progeny plant advantageously having all of the aforementioned resistances and the characteristics recited and tabulated herein, is preferred. Advantageously, the progeny plant demonstrates the traits of green leaves with a reddish purple petiole and midrib, slow growing, resistance to downy mildew (*Peronospora farinosa* f. sp. *betae*), a dark to very dark green leaf coloring and strongly blistered leaf blades and has genetic material for so exhibiting the combination of traits; wherein the genetic information is as contained in a plant, representative seed of which having been deposited under NCIMB Accession No. 42561.

Progeny of the hybrid Swiss chard variety 69-104 RZ may be modified in one or more other characteristics, in which the modification is a result of, for example and without limitation, mutagenesis or transformation with a transgene.

In another embodiment the invention relates to a method of producing a Swiss chard plant derived from a plant of the invention of which representative seed has been deposited under NCIMB Accession No. 42561, which may comprise of the steps: a) preparing a progeny plant derived from hybrid Swiss chard variety 69-104 RZ by crossing a Swiss chard plant exhibiting a combination of traits including green leaves with a reddish purple petiole and midrib, slow growing, resistance to downy mildew (*Peronospora farinosa* f. sp. *betae*), a dark to very dark green leaf coloring and strongly blistered leaf blades, representative seed of which have been deposited under NCIMB Accession No. 42561 with itself or a second Swiss chard plant; b) crossing the progeny plant with itself or a second Swiss chard plant to produce a seed of a progeny plant of a subsequent generation; c) growing a progeny plant of a subsequent generation from said seed and crossing the progeny plant of a subsequent generation with itself or a second Swiss chard plant; and d) repeating step b) or c) for at least 3 more generations to produce an inbred Swiss chard plant derived from the hybrid Swiss chard variety 69-104 RZ. In one embodiment the Swiss chard plant produced by this method is an inbred Swiss chard plant.

The invention even further relates to a method of producing Swiss chard leaves which may comprise: (a) obtaining a plant of hybrid Swiss chard variety 69-104 RZ, representative seed of which having been deposited under NCIMB Accession No. 42561, wherein the plant has been cultivated to obtain leaves (b) harvesting Swiss chard leaves from the plant to thereby obtain harvested Swiss chard leaves, and (c) optionally using the harvested Swiss chard leaves as a fresh vegetable or (d) optionally using the harvested Swiss chard leaves as a processed food. The harvested Swiss chard leaves of step (c) or step (d) may optionally have undergone one or more processing steps. Such a processing step might comprise but is not limited to any one of the following treatments or combinations thereof: cutting, washing, blanching, cooking, steaming, baking, pasteurizing, or freezing. The processed form that is obtained is also part of this invention. The invention further comprehends packaging the Swiss chard leaves in fresh or processed form.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP § 2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on 18

Mar. 2016, under deposit Accession Number NCIMB 42561 was made pursuant to the terms of the Budapest Treaty. Upon issuance of a patent, all restrictions upon the deposit will be removed, and the deposit is intended to meet the requirements of 37 CFR § 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention provides methods and compositions relating to plants, seeds and derivatives of a new hybrid Swiss chard variety herein referred to as hybrid Swiss chard variety 69-104 RZ. 69-104 RZ is a hybrid plant variety that is uniform and distinct from other such hybrids, and can be stably produced after a cycle of reproduction.

There are numerous steps in the development of any novel, plant with desirable characteristics. Selection of traits is a very important aspect of plant breeding. Once desirable traits are identified, the plants with those desirable traits are crossed in order to recombine the desirable traits and through selection, varieties or parent lines are developed. The goal is to combine in a single variety or hybrid an improved combination of desirable traits from the parent plant. These important traits may include but are not limited to higher yield, field performance, fruit and agronomic quality such as fruit shape, color and length, resistance to diseases and insects, and tolerance to drought and heat.

Choice of breeding or selection methods depends on the mode of plant reproduction, the heritability of the trait(s) being improved, and the type of cultivar used commercially (e.g., F1 hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach is used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The development of commercial Swiss chard hybrids relates to the development of Swiss chard parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics. For the production of Swiss chard hybrids male sterile mother lines are used.

Pedigree breeding is used commonly for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

An efficient way to establish a female line for hybrid seed production is to identify or create a line that is unable to produce viable pollen. Since this male-sterile line cannot self-pollinate, seed formation is dependent upon pollen from the male line. Cytoplasmic male sterility (CMS) is an example of such a mechanism used in hybrid seed production. In this case, the sterility is transmitted only through the female and all progeny will be sterile, unless a nuclear restorer gene is present. This is not a problem for crops such as Swiss chard where the product harvested from the hybrid is produced during vegetative growth. While CMS is controlled by an extranuclear genome, nuclear genes may have the capability to restore fertility. When nuclear restorer genes are available for a CMS system in a crop, it's called a cytoplasmic—genetic male sterility system. In that case the sterility is manifested by the influence of both nuclear (with Mendelian inheritance) and cytoplasmic (maternally inherited) genes. Cytoplasmic—genetic male sterility systems are widely used in crop plants for hybrid breeding due to the convenience of controlling sterility expression by manipulating the gene—cytoplasm combinations in any selected genotype (Schnable and Wise, Trends Plant Sci.

3:175-180, 1998). The skilled artisan knows how to work with a cytoplasmic-genetic male sterility system in plant breeding and is able to make progeny plants of plants of a hybrid variety and/or hybrid variety derived plants.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs)

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SNP technology is currently the most efficient and practical marker technology to identify the unique genetic composition of the invention and progeny varieties retaining that unique genetic composition (Mammadov, J. et al., Int. J. Plant Genomics 2012: 728398). SSR technology may also be used; more marker loci may be routinely used and more alleles per marker locus may be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection.

Molecular markers may also be used to identify and exclude certain sources of germplasm as parental varieties or ancestors of a plant by providing a means of tracking genetic profiles through crosses.

Mutation breeding is another method of introducing new traits into Swiss chard varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of double haploids may also be used for the development of homozygous lines in a breeding program. Double haploids are produced by the doubling of a set of chromosomes from a heterozygous plant to produce a completely homozygous individual. For example, see Wan et al., Theor. Appl. Genet., 77:889-892, 1989.

The Swiss chard plant of the invention may be arrived at through crossing of inbred lines or through selection of the disclosed desirable characteristics by any of the breeding the selection methods mentioned above.

The parents of hybrid Swiss chard variety 69-104 RZ were developed as follows: The mother is a Swiss chard line made from pedigree selection from CMS line no. S 08.87041. In total three selection and back-crossing cycles and one round of mass generation back-crossing was performed. The father line of 69-104 RZ is made from pedigree selection from no. S 08.89127, obtained by four selection and inbreeding cycles, and one round of mass generation and selection. Crossing the described mother and father inbred Swiss chard lines with one another will yield uniform F1 hybrid progeny plants. Table 1 shows the pedigree scheme of the mother line of hybrid Swiss chard 69-104 RZ, Table 2 shows the pedigree scheme of the father line of hybrid Swiss chard variety 69-104 RZ.

TABLE 1

Breeding history of the mother line of 69-104 RZ.

| Year | | |
|---|---|---|
| Year 1 | F1 | pedigree selection from S 08.87041 |
| Year 2 | BC1 F1 | generation grown |
| Year 3 | BC2 F1 | generation grown |
| Year 4 | BC3 F1 | generation grown (in mass) |

TABLE 2

Breeding history of the father line of 69-104 RZ.

| Year | | |
|---|---|---|
| Year 1 | F1 | pedigree selection from S 08.89127 |
| Year 2 | S1F1 | generation grown |
| Year 3 | S2F1 | generation grown |

TABLE 2-continued

Breeding history of the father line of 69-104 RZ.

| Year | | |
|---|---|---|
| Year 4 | S3F1 | generation grown |
| Year 5 | M1S3F1 | generation grown (in mass) |

In one embodiment, a plant of the invention has all the morphological and physiological characteristics of Swiss chard variety 69-104 RZ. These characteristics of a Swiss chard plant of the invention, e.g. variety 69-104 RZ, are summarized and compared to its closest publicly available variety in Table 3.

The information presented in Table 3 was determined in trial experiments in accordance with the UPOV TG/106/4 Form (Guidelines for the Conduct of Tests for Distinctness, Uniformity and Stability, International Union for the Protection of New Varieties of Plants). The terminology used in these tables is the official terminology found and defined in the UPOV TG/106/4 as of the filing date, and is thus clear for a person skilled in the art. The only change that was made in the terminology of Table 3 compared to the official terminology found in the UPOV TG/106/4 Form is the change of anthocyanin to betalain, as said UPOV Form incorrectly indicates the red coloration in Swiss chard tissues as anthocyanin coloration, while anthocyanin pigment does not occur in *Beta* species and the yellow to purple coloring of Swiss chard tissues is due to the presence of betalain pigments instead.

TABLE 3

Physiological and morphological characteristics of hybrid Swiss chard variety 69-104 RZ in comparison with closest known variety, the hybrid Swiss chard variety "Charlie RZ".

| Character | 69-104 RZ | Charlie RZ |
|---|---|---|
| Ploidy | Diploid | Diploid |
| Seedling | | |
| 1. Betalain* coloration | Present (9) | Present (9) |
| 2. Intensity of betalain* coloration | Strong (7) | Strong (7) |
| Leaf | | |
| 3. Length | Medium to long (6-7) | Long (7) |
| 4. Attitude | Semi-erect (3) | Semi-erect (3) |
| Leaf blade | | |
| 5. Length | Short (3) | Long (7) |
| 6. Width | Medium to broad (6) | Broad (7) |
| 7. Intensity of green color | Dark to very dark (8) | Medium to dark (6) |
| 8. Reflexing of margin | Medium to strong (6) | Weak (3) |
| 9. Glossiness | Strong (7) | Strong (7) |
| 10. Blistering | Medium to strong (6) | Medium to strong (6) |
| 11. Betalain* coloration | Present (9) | Present (9) |
| 12. Intensity of betalain* coloration | Medium (5) | Weak to medium (4) |
| Petiole | | |
| 13. Length | Medium to long (6) | Long to very long (8) |
| 14. Width | Medium to broad (6) | Narrow (3) |
| 15. Curvature of inner side of cross section | Very weak to weak (2) | Weak (3) |
| 16. Color | Purple (5) | Purple (5) |
| 17. Time of beginning of bolting | Early to medium (4) | Early to medium (4) |

Aside from the morphological and physiological characteristics mentioned in Table 3, a plant of the invention also exhibits green leaves with a reddish purple petiole and midrib, slow growing, resistance to downy mildew (*Peronospora farinosa* f sp. *betae*), a dark to very dark green leaf coloring and strongly blistered leaf blades.

Swiss chard variety 69-104 RZ has green leaves with a reddish purple petiole and midrib. Depending on growing conditions the growth speed of the plants may vary causing variation in the coloration of the secondary veins of the green leaf blade of hybrid Swiss chard variety 69-104 RZ. Plants having a very high growth speed may show less reddish purple coloring of the secondary veins of the green leaf blade of Swiss chard variety 69-104 RZ. Said reddish purple color is categorized as purple using the official terminology of the UPOV TG/106/4 Form, but may also be indicated as red. The reddish purple color of the petiole and midrib of the green leaf blade of leaves of hybrid Swiss chard variety 69-104 RZ is similar to that of its closest available variety Charlie RZ, though the reddish purple color is slightly more intense in 69-104 RZ compared to Charlie RZ.

As used herein, growth speed is determined by comparison to publicly available varieties. Slow growing is defined as growing at a growth speed that is slower than that of publicly available Swiss chard variety Charlie RZ and growing at a growth speed that is higher than that of publicly available Swiss chard cultivar Rhubarb. Hybrid Swiss chard variety 69-104 RZ is a slow growing Swiss chard variety which has a growth speed that is slower than that of publicly available Swiss chard variety Charlie RZ and higher than that of publicly available Swiss chard cultivar Rhubarb.

As used herein, resistance to *Peronospora farinosa* f. sp. *betae* is defined as the ability of a plant to resist infection by *Peronospora farinosa* f. sp. *betae*. Resistance is tested by inoculating plants with *Peronospora farinosa* f sp. *betae* at the true leaf stage and observing symptoms of downy mildew infection, including leaf spots and sporulation, 6 and 13 days after inoculation. Resistant plants show no symptoms of downy mildew infection. Hybrid Swiss chard variety 69-104 RZ exhibits a resistance to *Peronospora farinosa* f sp. *betae*, and does not show sporulation upon infection with *Peronospora farinosa* f sp. *betae*.

As used herein, the blistering of the leaf blade is by visual comparison to standard varieties at the stage when the foliage has reached its maximum height. Three different levels of blistering of the leaf blade are recognized: weak, medium or strong. Leaf blade blistering is determined by comparison to standard varieties Groene Gewone, Blonde à carde blanche, Paros and Lucullus at the stage when the foliage has reached its maximum height. Groene Gewone has weakly blistered leaf blades, Blonde à carde blanche and Paros have medium blistered leaf blades, while Lucullus has strongly blistered leaf blades. Hybrid Swiss chard variety 69-104 RZ has strongly blistered leaf blades which is similar to Lucullus. Hybrid Swiss chard variety 69-104 RZ has a strong blistering of the leaf blade.

As used herein, the intensity of the green color of the leaf blade is determined by comparison to publicly available varieties. Dark to very dark green leaf coloring is defined as having an intensity of the green color of the leaf blade comparable to that of publicly available Swiss chard variety Compacta Slo bolt and darker than that of publicly available variety Fordhook Giant. Hybrid Swiss chard variety 69-104 RZ has a dark to very dark green leaf coloring which has an intensity of the green color of the leaf blade that is comparable to that of publicly available variety Compacta Slo bolt and that is darker than that of publicly available variety Fordhook Giant.

In an embodiment, the invention relates to Swiss chard plants that have all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits may be introduced into a hybrid by backcrossing the trait into one or both parents, useful traits may be introduced directly into the plant of the invention, being a plant of hybrid Swiss chard variety 69-104 RZ, by genetic transformation techniques; and, such plants of hybrid Swiss chard variety 69-104 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of hybrid Swiss chard variety 69-104 RZ or may, alternatively, be used for the preparation of transgenes which may be introduced by backcrossing. Methods for the transformation of plants, including Swiss chard, are well known to those of skill in the art.

Vectors used for the transformation of Swiss chard cells are not limited so long as the vector may express an inserted DNA in the cells. For example, vectors which may comprise promoters for constitutive gene expression in Swiss chard cells (e.g., cauliflower mosaic virus 35S promoter) and promoters inducible by exogenous stimuli may be used. Examples of suitable vectors include pBI binary vector. The "Swiss chard cell" into which the vector is to be introduced includes various forms of Swiss chard cells, such as cultured cell suspensions, protoplasts, leaf sections, and callus. A vector may be introduced into Swiss chard cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target Swiss chard cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of Swiss chard variety 69-104 RZ.

*Agrobacterium*-mediated transfer is another widely applicable system for introducing gene loci into plant cells. An advantage of the technique is that DNA may be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes may be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including Swiss chard plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for Swiss chard plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins (psaD, psaF, psaE, PC, FNR, atpC, atpD, cab, rbcS) (see U.S. Pat. No. 7,161,061), the CAB-1 promoter (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5)

chemicals such as methyl jasmonate, salicylic acid, or Safener. It may also be advantageous to employ organ-specific promoters.

Exemplary nucleic acids which may be introduced to the Swiss chard variety of this invention include, for example, DNA sequences or genes from another species, or even genes or sequences which originate with or are present in Swiss chard species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of Swiss chard variety 69-104 RZ. Non-limiting examples of particular genes and corresponding phenotypes one may choose to introduce into a Swiss chard plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed Swiss chard and/or methods of transforming Swiss chard or Swiss chard plant cells, and techniques from these US patents, as well as promoters, vectors, etc., may be employed in the practice of this invention to introduce exogenous nucleic acid sequence(s) into a plant of Swiss chard variety 69-104 RZ (or cells thereof), and exemplify some exogenous nucleic acid sequence(s) which may be introduced into a plant of Swiss chard variety 69-104 RZ (or cells thereof) of the invention, as well as techniques, promoters, vectors etc., to thereby obtain further plants of Swiss chard variety 69-104 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention relates to a method of producing a plant of Swiss chard hybrid variety 69-104 RZ which may comprise at least one new trait, the method may comprise introducing a mutation or transgene conferring the at least one new trait into a plant of hybrid Swiss chard variety 69-104 RZ, wherein a sample of seed of said variety has been deposited under NCIMB Accession Number 42561. The invention further relates to a Swiss chard plant produced by said method.

The invention relates to a plant of hybrid Swiss chard variety 69-104 RZ which may comprise a transgene conferring a desired trait, a sample of seed of said variety has been deposited under NCIMB Accession Number 42561. The invention also relates to a seed that produces said plant.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems (See generally U.S. Pat. No. 5,969,215 on Swiss chard being recognized as a plant that may be regenerated from cultured cells or tissue).

The invention further relates to a method for producing a Swiss chard seed, which may comprise crossing the plant grown from the seed of hybrid Swiss chard variety 69-104 RZ, a sample of seed of said hybrid variety having been deposited under NCIMB Accession No. 42561, with itself or a second Swiss chard plant. The invention further relates to a Swiss chard seed produced by said method, and to a Swiss chard plant grown from said Swiss chard seed.

Also, the invention comprehends methods for producing a seed of a 69-104 RZ-derived Swiss chard plant which may comprise (a) crossing a plant of Swiss chard variety 69-104 RZ, representative seed of which having been deposited under NCIMB Accession No. 42561, with a second Swiss chard plant or with itself, and (b) allowing seed of a 69-104 RZ-derived Swiss chard plant to form. Such a method may further comprise (c) selfing the plant grown from said hybrid variety 69-104 RZ-derived Swiss chard seed or crossing it to a second Swiss chard plant to yield additional hybrid variety 69-104 RZ-derived Swiss chard seed; (d) growing said additional hybrid variety 69-104 RZ-derived Swiss chard seed of step (c) to yield additional 69-104 RZ-derived Swiss chard plants; and (e) repeating the crossing and growing steps of (c) and (d) for an additional 3-10 generations to generate further 69-104 RZ-derived Swiss chard plants, and (f) allowing seed of a hybrid variety 69-104 RZ-derived Swiss chard plant to form.

The invention further relates to the above methods that may further comprise selecting at steps b), d), and e), a "69-104 RZ"-derived Swiss chard plant exhibiting a combination of traits including green leaves with a reddish purple petiole and midrib, slow growing, resistance to downy mildew (*Peronospora farinosa* f. sp. *betae*), a dark to very dark green leaf coloring and strongly blistered leaf blades.

The invention further relates to a Swiss chard seed produced by the above described methods, and to a Swiss chard plant grown from said Swiss chard seed.

Backcrossing one of the parents of a hybrid may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The invention further involves a method of determining the genotype of a plant of hybrid Swiss chard variety 69-104 RZ, representative seed of which has been deposited under NCIMB Accession Number 42561, or a first generation progeny thereof, which may comprise obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of hybrid Swiss chard variety 69-104 RZ and/or give rise to the expression of any one or more, or all, of the morphological and physiological characteristics of hybrid Swiss chard variety 69-104 RZ.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used a fingerprint may be obtained that is unique for hybrid Swiss chard variety 69-104 RZ. Obtaining a unique DNA fingerprint depends on the genetic variation present in a variety and the sensitivity of the fingerprinting technique. A technique known in the art to provide a good fingerprint profile is called the AFLP fingerprinting technique (See generally U.S. Pat. No. 5,874,215), but there are many other marker-based techniques, such as RFLP (or Restriction fragment length polymorphism), SSLP (or Simple sequence length polymorphism), RAPD (or Random amplification of polymorphic DNA), VNTR (or Variable number tandem repeat), Microsatellite polymorphism, SSR (or Simple sequence repeat), STR (or Short tandem repeat), SFP (or Single feature polymorphism), DArT (or Diversity Arrays Technology), RAD markers (or Restriction site associated DNA markers) (e.g. Semagn et al. African Journal of Biotechnology Vol. 5 number 25 pp. 2540-2568, 29 Dec., 2006; Baird et al. PloS ONE Vol. 3 number 10 e3376, 2008). Nowadays, sequence-based methods are utilising Single Nucleotide Polymorphisms (SNPs) that are randomly distributed across genomes, as a common tool for genotyping (eg. Elshire et al. PloS ONE Vol. 6 number 5 e19379, 2011; Poland et al. PloS ONE Vol. 7 number 2 e32253, 2012; Truong et al. PloS ONE Vol. 7 number 5 e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. It is possible, for example, to detect polymorphisms for the characteristic of resistance to *Peronospora farinosa* f. sp. *betae* by comparing the genotype and/or the sequence of Swiss chard variety 69-104 RZ with the genotype and/or the sequence of one or more reference plants. The reference plant(s) used for comparison may for example be, but is not limited to Fordhook Giant. It is also possible for example, to detect polymorphisms for resistance to *Peronospora farinosa* f. sp. *betae* by comparing the genotype and/or the sequence of Swiss chard variety 69-104 RZ with the genotype and/or the sequence of one or more reference plants. The reference plant(s) used for comparison may for example be, but is not limited to, the comparison variety Charlie RZ.

The polymorphisms revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

Swiss chard leaves are sold in packaged form, including without limitation as pre-packaged Swiss chard salad or as canned Swiss chard or as frozen Swiss chard. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the Swiss chard leaves of the invention. Thus, the invention comprehends the use of and methods for making and using the leaves of the Swiss chard of the invention, as well as leaves of Swiss chard derived from the invention.

The invention further relates to a container which may comprise one or more plants of the invention, or one or more Swiss chard plants derived from a plant of the invention, in a growth substrate for harvest of leaves from the plant in a domestic environment. This way the consumer may pick very fresh leaves for use in salads. More generally, the invention includes one or more plants of the invention or one or more plants derived from Swiss chard of the invention, wherein the plant is in a ready-to-harvest condition, including with the consumer picking his own, and further including a container which may comprise one or more of these plants.

The invention is further described by the following numbered paragraphs:

1. A seed of hybrid Swiss chard variety 69-104 RZ, a sample of seed of said hybrid variety having been deposited under NCIMB Accession Number 42561.

2. A plant grown from the seed of paragraph 1.

3. The Swiss chard plant of paragraph 2, which is a plant grown from seed having been deposited under NCIMB Accession Number 42561.

4. A Swiss chard plant, or a part thereof, having all the physiological and morphological characteristics of the Swiss chard plant of paragraph 2.

5. A part of the plant of paragraph 2, wherein said part is a microspore, pollen, an ovary, an ovule, an embryo sac, an egg cell, a cutting, a root, a stem, a cell or a protoplast.

6. A tissue culture of regenerable cells or protoplasts from the plant part of paragraph 5.

7. The tissue culture of paragraph 6, wherein said cells or protoplasts of the tissue culture are derived from a leaf, pollen, an embryo, a cotyledon, a hypocotyl, a meristematic cell, a root, a root tip, an anther, a flower, a seed or a stem.

8. A Swiss chard plant regenerated from the tissue culture of paragraph 6, wherein the regenerated plant expresses all of the physiological and morphological characteristics of hybrid Swiss chard variety 69-104 RZ, a sample of seed of said hybrid having been deposited under NCIMB Accession Number 42561.

9. A method of vegetatively propagating a plant of hybrid Swiss chard variety 69-104 RZ comprising the steps of: (a) collecting tissue capable of being propagated from a plant of hybrid Swiss chard variety 69-104 RZ, representative seed of said hybrid Swiss chard variety having been deposited under NCIMB Accession Number 42561; and (b) producing a rooted plant from said tissue.

10. A method of producing a Swiss chard seed, comprising crossing the plant of paragraph 2 with itself or a second Swiss chard plant.

11. A Swiss chard seed produced by the method of paragraph 10.

12. A Swiss chard plant grown from the seed of paragraph 11.

13. A method for producing a seed of a hybrid Swiss chard variety 69-104 RZ-derived Swiss chard plant comprising the steps of: (a) crossing a Swiss chard plant of hybrid variety 69-104 RZ, representative seed of which having been deposited under NCIMB Accession Number 42561, with a second Swiss chard plant or with itself; and (b) allowing seed of a hybrid variety 69-104 RZ-derived Swiss chard plant to form.

14. The method of paragraph 13, further comprising the steps of: (c) selfing the plant grown from said hybrid variety 69-104 RZ-derived Swiss chard seed or crossing it to a second Swiss chard plant to yield additional hybrid variety 69-104 RZ-derived Swiss chard seed; (d) growing said additional hybrid variety 69-104 RZ-derived Swiss chard seed of step (c) to yield additional 69-104 RZ-derived Swiss chard plants; and (e) repeating the crossing and growing steps of (c) and (d) for an additional 3-10 generations to generate further 69-104 RZ-derived Swiss chard plants, and (f) allowing seed of a hybrid variety 69-104 RZ-derived Swiss chard plant to form.

15. A Swiss chard seed produced by the method of paragraphs 13 or 14.

16. A Swiss chard plant grown from the seed of paragraph 15.

17. A method of producing a plant of Swiss chard hybrid variety 69-104 RZ comprising at least one new trait, the method comprising introducing a mutation or transgene conferring the at least one new trait into a plant of hybrid Swiss chard variety 69-104 RZ, wherein a sample of seed of said variety has been deposited under NCIMB Accession Number 42561.

18. The Swiss chard plant produced by the method of paragraph 17.

19. A method of producing Swiss chard leaves comprising: (a) obtaining a plant according to paragraph 2, wherein the plant has been cultivated to obtain leaves; and (b) harvesting Swiss chard leaves from the plant to thereby obtain harvested Swiss chard leaves.

20. The method of paragraph 19 further comprising packaging the harvested Swiss chard leaves as a fresh vegetable.

21. The method of paragraph 19 further comprising processing the harvested Swiss chard leaves as a processed food.

22. A container comprising one or more Swiss chard plants of paragraph 2 for harvest of leaves.

23. A method of determining the genotype of a plant of hybrid Swiss chard variety 69-104 RZ, representative seed of which has been deposited under NCIMB Accession Number 42561, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of hybrid Swiss chard variety 69-104 RZ and/or give rise to the expression of any one or more, or all, of the morphological and physiological characteristics of hybrid Swiss chard variety 69-104 RZ.

24. A plant of Swiss chard hybrid variety 69-104 RZ comprising a transgene conferring a desired trait, a sample of seed of said variety has been deposited under NCIMB Accession Number 42561.

25. A seed that produces the plant of paragraph 24.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A seed of hybrid Swiss chard variety 69-104 RZ, a sample of seed of said hybrid variety having been deposited under NCIMB Accession Number 42561.

2. A plant grown from the seed of claim 1.

3. The Swiss chard plant of claim 2, which is a plant grown from seed having been deposited under NCIMB Accession Number 42561.

4. A Swiss chard plant, or a part thereof, having all the physiological and morphological characteristics of the Swiss chard plant of claim 2.

5. A part of the plant of claim 2, wherein said part is an ovary, an embryo sac, an egg cell, a cutting, a root, a stem, a cell or a protoplast.

6. A tissue culture of regenerable cells or protoplasts from the plant part of claim 5.

7. The tissue culture as claimed in claim 6, wherein said cells or protoplasts of the tissue culture are derived from a leaf, pollen, an embryo, a cotyledon, a hypocotyl, a meristematic cell, a root, a root tip, an anther, a flower, a seed or a stem.

8. A Swiss chard plant regenerated from the tissue culture of claim 6, wherein the regenerated plant expresses all of the physiological and morphological characteristics of hybrid Swiss chard variety 69-104 RZ, a sample of seed of said hybrid having been deposited under NCIMB Accession Number 42561.

9. A method of vegetatively propagating a plant of hybrid Swiss chard variety 69-104 RZ comprising the steps of: (a) collecting tissue capable of being propagated from a plant of hybrid Swiss chard variety 69-104 RZ, representative seed of said hybrid Swiss chard variety having been deposited under NCIMB Accession Number 42561; and (b) producing a rooted plant from said tissue.

10. A method of producing a Swiss chard seed, comprising crossing the plant of claim 2 with itself or a second Swiss chard plant.

11. A Swiss chard seed produced by the method of claim 10, wherein a plant grown from said seed has all of the physiological and morphological characteristics of hybrid Swiss chard variety 69-104 RZ, a sample of seed of said hybrid having been deposited under NCIMB Accession Number 42561.

12. A Swiss chard plant grown from the seed as claimed in claim 11, which plant has all of the physiological and morphological characteristics of hybrid Swiss chard variety 69-104 RZ, a sample of seed of said hybrid having been deposited under NCIMB Accession Number 42561.

13. A method for producing a seed of a hybrid Swiss chard variety 69-104 RZ-derived Swiss chard plant comprising the steps of: (a) crossing a Swiss chard plant of hybrid variety 69-104 RZ, representative seed of which having been deposited under NCIMB Accession Number 42561, with a second Swiss chard plant or with itself; and (b) allowing seed of a hybrid variety 69-104 RZ-derived Swiss chard plant to form.

14. The method of claim 13, further comprising the steps of: (c) selfing the plant grown from said hybrid variety 69-104 RZ-derived Swiss chard seed or crossing it to a second Swiss chard plant to yield additional hybrid variety 69-104 RZ-derived Swiss chard seed; (d) growing said additional hybrid variety 69-104 RZ-derived Swiss chard seed of step (c) to yield additional 69-104 RZ-derived Swiss chard plants; and (e) repeating the crossing and growing steps of (c) and (d) for an additional 3-10 generations to generate further 69-104 RZ-derived Swiss chard plants, and (f) allowing seed of a hybrid variety 69-104 RZ-derived Swiss chard plant to form.

15. A Swiss chard seed produced by the method of claim 13 or 14, wherein a plant grown from said seed has all of the physiological and morphological characteristics of hybrid Swiss chard variety 69-104 RZ, a sample of seed of said hybrid having been deposited under NCIMB Accession Number 42561.

16. A Swiss chard plant grown from the seed of claim 15, which plant has all of the physiological and morphological characteristics of hybrid Swiss chard variety 69-104 RZ, a sample of seed of said hybrid having been deposited under NCIMB Accession Number 42561.

17. A method of producing a plant of Swiss chard hybrid variety 69-104 RZ comprising at least one new trait, the method comprising introducing a mutation or transgene conferring the at least one new trait into a plant of hybrid Swiss chard variety 69-104 RZ, wherein a sample of seed of said variety has been deposited under NCIMB Accession Number 42561.

18. A method of producing Swiss chard leaves comprising: (a) obtaining a plant according to claim 2, wherein the plant has been cultivated to obtain leaves; and (b) harvesting Swiss chard leaves from the plant to thereby obtain harvested Swiss chard leaves.

19. The method of claim 18 further comprising packaging the harvested Swiss chard leaves as a fresh vegetable.

20. The method of claim 18 further comprising processing the harvested Swiss chard leaves as a processed food.

21. A container comprising one or more Swiss chard plants of claim 2 for harvest of leaves.

22. A method of determining the genotype of a plant of hybrid Swiss chard variety 69-104 RZ, representative seed of which has been deposited under NCIMB Accession Number 42561, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of hybrid Swiss chard variety 69-104 RZ and/or give rise to the expression of any one or more, or all, of the morphological and physiological characteristics of hybrid Swiss chard variety 69-104 RZ.

23. A plant of Swiss chard hybrid variety 69-104 RZ comprising a transgene conferring a desired trait, a sample of seed of said variety has been deposited under NCIMB Accession Number 42561.

24. A seed that produces the plant of claim 23.

* * * * *